US011022797B2

(12) United States Patent
Samec et al.

(10) Patent No.: US 11,022,797 B2
(45) Date of Patent: Jun. 1, 2021

(54) AUGMENTED REALITY PULSE OXIMETRY

(71) Applicant: Magic Leap Inc., Plantation, FL (US)

(72) Inventors: Nicole Elizabeth Samec, Ft. Lauderdale, FL (US); Adrian Kaehler, San Francisco, CA (US)

(73) Assignee: Magic Leap, Inc., Plantation, FL (US)

( * ) Notice: Subject to any disclaimer, the term of this patent is extended or adjusted under 35 U.S.C. 154(b) by 1104 days.

(21) Appl. No.: 15/072,341

(22) Filed: Mar. 16, 2016

(65) Prior Publication Data

US 2016/0287153 A1 Oct. 6, 2016

Related U.S. Application Data

(60) Provisional application No. 62/133,870, filed on Mar. 16, 2015.

(51) Int. Cl.
*A61B 5/1455* (2006.01)
*G02B 27/01* (2006.01)
(Continued)

(52) U.S. Cl.
CPC .......... *G02B 27/0172* (2013.01); *A61B 3/005* (2013.01); *A61B 3/0008* (2013.01);
(Continued)

(58) Field of Classification Search
CPC .............. A61B 5/1455; A61B 5/14551; A61B 5/14552; A61B 5/14555; A61B 5/6803; A61B 5/6821; A61B 2562/0238
See application file for complete search history.

(56) References Cited

U.S. PATENT DOCUMENTS 4,807,631 A * 2/1989 Hersh ................ A61B 5/14551
600/323
4,869,253 A * 9/1989 Craig, Jr. ........... A61B 5/14551
600/323
(Continued)

FOREIGN PATENT DOCUMENTS

JP 2004-167080 A 6/2004
JP 2008-099834 A 5/2008
JP 2013-59469 A 4/2013

OTHER PUBLICATIONS

"Extended European Search Report dated Sep. 27, 2018", European Patent Application No. 16765702.2 , (8 pages).
(Continued)

*Primary Examiner* — Eric F Winakur
(74) *Attorney, Agent, or Firm* — Stephen M. De Klerk

(57) ABSTRACT

One embodiment is directed to a system comprising a head-mounted member removably coupleable to the user's head; one or more electromagnetic radiation emitters coupled to the head-mounted member and configured to emit light with at least two different wavelengths toward at least one of the eyes of the user; one or more electromagnetic radiation detectors coupled to the head-mounted member and configured to receive light reflected after encountering at least one blood vessel of the eye; and a controller operatively coupled to the one or more electromagnetic radiation emitters and detectors and configured to cause the one or more electromagnetic radiation emitters to emit pulses of light while also causing the one or more electromagnetic radiation detectors to detect levels of light absorption related to the emitted pulses of light, and to produce an output that is proportional to an oxygen saturation level in the blood vessel.

17 Claims, 8 Drawing Sheets

(51) Int. Cl.

| | | |
|---|---|---|
| A61B 3/14 | (2006.01) | |
| A61B 3/113 | (2006.01) | |
| A61B 3/16 | (2006.01) | |
| G06T 19/00 | (2011.01) | |
| A61B 3/10 | (2006.01) | |
| G16H 40/63 | (2018.01) | |
| G16H 40/67 | (2018.01) | |
| A61B 5/145 | (2006.01) | |
| A61M 21/02 | (2006.01) | |
| A61B 3/00 | (2006.01) | |
| A61B 3/12 | (2006.01) | |
| A61B 5/361 | (2021.01) | |
| A61B 5/369 | (2021.01) | |
| A61B 5/398 | (2021.01) | |
| A61B 5/00 | (2006.01) | |
| A61B 8/10 | (2006.01) | |
| A61B 8/00 | (2006.01) | |
| A61B 3/08 | (2006.01) | |
| A61B 3/103 | (2006.01) | |
| A61F 9/00 | (2006.01) | |
| G02B 27/00 | (2006.01) | |
| A61B 3/028 | (2006.01) | |
| A61B 3/06 | (2006.01) | |
| A61B 3/02 | (2006.01) | |
| A61B 3/13 | (2006.01) | |
| G02B 21/00 | (2006.01) | |
| A61B 3/024 | (2006.01) | |
| A61B 5/01 | (2006.01) | |
| A61M 21/00 | (2006.01) | |
| G02C 7/02 | (2006.01) | |
| A61F 7/00 | (2006.01) | |
| A61N 5/06 | (2006.01) | |
| A61F 9/008 | (2006.01) | |

(52) U.S. Cl.
CPC ............ *A61B 3/0025* (2013.01); *A61B 3/022* (2013.01); *A61B 3/024* (2013.01); *A61B 3/028* (2013.01); *A61B 3/063* (2013.01); *A61B 3/066* (2013.01); *A61B 3/08* (2013.01); *A61B 3/085* (2013.01); *A61B 3/10* (2013.01); *A61B 3/102* (2013.01); *A61B 3/1005* (2013.01); *A61B 3/1015* (2013.01); *A61B 3/1035* (2013.01); *A61B 3/113* (2013.01); *A61B 3/12* (2013.01); *A61B 3/1216* (2013.01); *A61B 3/1241* (2013.01); *A61B 3/13* (2013.01); *A61B 3/14* (2013.01); *A61B 3/165* (2013.01); *A61B 5/0059* (2013.01); *A61B 5/1455* (2013.01); *A61B 5/14532* (2013.01); *A61B 5/14555* (2013.01); *A61B 5/361* (2021.01); *A61B 5/369* (2021.01); *A61B 5/398* (2021.01); *A61B 5/6803* (2013.01); *A61B 8/10* (2013.01); *A61B 8/461* (2013.01); *A61F 9/0026* (2013.01); *A61M 21/02* (2013.01); *G02B 21/0032* (2013.01); *G02B 27/0093* (2013.01); *G02B 27/0179* (2013.01); *G06T 19/006* (2013.01); *G16H 40/63* (2018.01); *G16H 40/67* (2018.01); *A61B 5/0066* (2013.01); *A61B 5/0077* (2013.01); *A61B 5/01* (2013.01); *A61B 2562/0204* (2013.01); *A61B 2562/0219* (2013.01); *A61B 2562/0247* (2013.01); *A61F 2007/0004* (2013.01); *A61F 2007/004* (2013.01); *A61F 2009/00863* (2013.01); *A61H 2201/165* (2013.01); *A61M 2021/0022* (2013.01); *A61M 2021/0027* (2013.01); *A61M 2021/0066* (2013.01); *A61M 2205/3375* (2013.01); *A61M 2205/507* (2013.01); *A61N 2005/0648* (2013.01); *G02B 2027/014* (2013.01); *G02B 2027/0138* (2013.01); *G02B 2027/0185* (2013.01); *G02C 7/027* (2013.01); *G06T 2207/10024* (2013.01); *G06T 2207/10148* (2013.01); *G06T 2207/10152* (2013.01); *G06T 2207/30041* (2013.01)

(56) References Cited

U.S. PATENT DOCUMENTS

| | | | |
|---|---|---|---|
| 5,111,817 A * | 5/1992 | Clark | ............... A61B 5/14552 600/323 |
| 5,297,554 A | 3/1994 | Glynn et al. | |
| 5,348,005 A | 9/1994 | Merrick et al. | |
| 5,372,136 A * | 12/1994 | Steuer | ............... A61B 5/14535 600/326 |
| 6,477,394 B2 | 11/2002 | Rice et al. | |
| 7,488,294 B2 * | 2/2009 | Torch | ................... A61B 3/0066 600/558 |
| 8,911,087 B2 * | 12/2014 | Publicover | ........... A61B 5/6803 351/206 |
| 2002/0072658 A1 | 6/2002 | Rice et al. | |
| 2004/0054269 A1 | 3/2004 | Rantala et al. | |
| 2007/0270673 A1 | 11/2007 | Abrams et al. | |
| 2010/0076281 A1 * | 3/2010 | Navon | ............... A61B 5/14535 600/323 |
| 2012/0316459 A1 | 12/2012 | Abreu | |
| 2013/0009993 A1 * | 1/2013 | Horseman | ............... G16H 40/63 345/633 |
| 2013/0066177 A1 | 3/2013 | Tone et al. | |
| 2014/0163329 A1 | 6/2014 | Brown, Jr. et al. | |
| 2014/0194708 A1 | 7/2014 | Ho et al. | |
| 2015/0038874 A1 | 2/2015 | Abreu | |
| 2015/0066000 A1 | 3/2015 | An et al. | |
| 2016/0022147 A1 * | 1/2016 | Kulcke | ............... A61B 5/14551 600/324 |
| 2016/0066847 A1 * | 3/2016 | Sales | ..................... A61B 5/1114 600/324 |

OTHER PUBLICATIONS

Abdulhalim, Ibrahim, "Liquid crystal devices tailored for specific imaging applications", SPIE: Newsroom, 10.1117/2.1201409. 005605, 2014, 4 pages.

Chan, Edward D. et al., "Pulse oximetry: Understanding its basic principles facilitates appreciation of its limitations", Elsevier, Respiratory Medicine (2013) 107, pp. 789-799.

Jacques, Steven L. , "Corrigendum: Optical properties of biological tissues: a review", 2013 Physics in Medicine and Biology 58 (2013) 5007-5008, 27 Pages.

Yim, D. et al., "On the Modeling of Light Interactions with Human Blood", Natural Phenomena Simulation Group, D.R. Cheriton School of Computer Science, University of Waterloo Technical Report CS-2011-30 Dec. 2011, pp. 1-19.

International Search Report and Written Opinion dated Jun. 10, 2016, International PCT Application No. PCT/US16/22724 with International Filing Date of Mar. 16, 2016, (10 pages).

Communication Pursuant to Article 94(3) EPC dated May 31, 2019, European Patent Application No. 16765702.2, (6 pages).

First Examination Report dated Jan. 3, 2020 with English translation, Chinese Patent Application No. 201680021671.3, (16 pages).

Notice of Reasons for Rejection dated Feb. 4, 2020 with English translation, Japanese Patent Application No. 2017-548443, (12 pages).

Final Office Action dated Sep. 30, 2020 with English translation, Japanese Patent Application No. 2017-548443, (7 pages).

First Examination Report dated Mar. 13, 2020, Australian Patent Application No. 2016233380, (6 pages).

(56) References Cited

OTHER PUBLICATIONS

Second Examination Report dated Aug. 17, 2020, Chinese Patent Application No. 201680021671.3, (15 pages).

* cited by examiner

AUGMENTED REALITY PULSE OXIMETRY

RELATED APPLICATION DATA

The present application claims the benefit under 35 U.S.C. § 119 to U.S. Provisional Application Ser. No. 62/133,870 filed Mar. 16, 2015. The foregoing application is hereby incorporated by reference into the present application in its entirety.

FIELD OF THE INVENTION

The present disclosure relates to systems and methods for augmented reality using wearable componentry, and more specifically to configurations for determining oxygen saturation in the blood of a user in the context of augmented reality systems.

BACKGROUND

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user.

For example, referring to FIG. 1, an augmented reality scene (4) is depicted wherein a user of an AR technology sees a real-world park-like setting (6) featuring people, trees, buildings in the background, and a concrete platform (1120). In addition to these items, the user of the AR technology also perceives that he "sees" a robot statue (1110) standing upon the real-world platform (1120), and a cartoon-like avatar character (2) flying by which seems to be a personification of a bumble bee, even though these elements (2, 1110) do not exist in the real world. As it turns out, the human visual perception system is very complex, and producing a VR or AR technology that facilitates a comfortable, natural-feeling, rich presentation of virtual image elements amongst other virtual or real-world imagery elements is challenging. For instance, head-worn AR displays (or helmet-mounted displays, or smart glasses) typically are at least loosely coupled to a user's head, and thus move when the user's head moves. If the user's head motions are detected by the display system, the data being displayed can be updated to take the change in head pose into account. Certain aspects of suitable AR systems are disclosed, for example, in U.S. patent application Ser. No. 14/205,126, entitled "System and method for augmented and virtual reality", which is incorporated by reference in its entirety herein, along with the following additional disclosures, which relate to augmented and virtual reality systems such as those developed by Magic Leap, Inc. of Fort Lauderdale, Fla.: U.S. patent application Ser. No. 14/641,376; U.S. patent application Ser. No. 14/555,585; U.S. patent application Ser. No. 14/212,961; U.S. patent application Ser. No. 14/690,401; U.S. patent application Ser. No. 13/663,466; U.S. patent application Ser. No. 13/684,489; and U.S. Patent Application Ser. No. 62/298,993, each of which is incorporated by reference herein in its entirety.

Such AR and VR systems typically comprise a processing capability, such as a controller or microcontroller, and also a power supply to power the function of the various components, and by virtue of the fact that at least some of the components in a wearable computing system, such as an AR or VR system, are close to the body of the user operating them, there is an opportunity to utilize some of these system components to conduct certain physiologic monitoring tasks relative to the user. Referring ahead to FIGS. 4A-4C, certain aspects of pulse oximetry are shown. Referring to FIG. 4A, a conventional pulse oximeter device (802) is configured to be temporarily coupled to a user's finger (804), ear lobe, or other similar tissue structure, and to pulse light at different wavelengths through such tissue structure while detecting transmission (and therefore absorption) at the other side of the tissue structure, to provide an output that is proportional to, or reads as, an estimated blood oxygen saturation level. Such devices are often used, for example, by high-altitude climbers or in healthcare scenarios. FIG. 4B illustrates a chart (810) of the absorption spectra of hemoglobin that is oxygenated (806) versus deoxygenated (808), and as shown in such plots (806, 808), in the red light wavelength range of the electromagnetic spectrum, such as around 660 nm, there is a notable difference in absorption for oxygenated versus deoxygenated hemoglobin, whereas there is an inverted difference at around 940 nm in the infrared wavelength range. Pulsing radiation at such wavelengths and detecting with a pulse oximeter is known to take advantage of such known absorption differences in the determination of oxygen saturation for the particular user. While pulse oximeters (802) typically are configured to at least partially encapsulate a tissue structure such as a finger (804) or ear lobe, certain desktop style systems have been suggested, such as that (812) depicted in FIG. 4C, to observe absorption differences in vessels of the eye, such as retinal vessels. Such a configuration (812) may be termed a flow oximetry system and comprise components as shown, including a camera (816), zoom lens (822), first (818) and second (820) light emitting diodes (LEDs), and one or more beam splitters (814). While it would be valuable to certain users, such as high-altitude hikers or persons with certain cardiovascular or respiratory problems, to be able to see a convenient display of their own blood oxygen saturation as the move about their day and conduct their activities, most configurations involve a somewhat inconvenient encapsulation of a tissue structure, or are not designed or well suited to be wearable. A solution is presented herein which combines the convenience of wearable computing in the form of an AR or VR system with the oxygen saturation monitoring technology of pulse oximetry.

SUMMARY OF THE INVENTION

One embodiment is directed to a system for determining oxygen saturation of a user, comprising: a head-mounted member removably coupleable to the user's head; one or more electromagnetic radiation emitters coupled to the head-mounted member and configured to emit light with at least two different wavelengths in the visible to infrared spectrum (or in another embodiment, in the non-visible to infrared spectrum) in direction of at least one of the eyes of the user; one or more electromagnetic radiation detectors coupled to the head-mounted member and configured to receive light reflected after encountering at least one blood vessel of the eye of the user; and a controller operatively coupled to the one or more electromagnetic radiation emitters and one or more electromagnetic radiation detectors and configured to cause the one or more electromagnetic radiation emitters to emit pulses of light while also causing the one or more electromagnetic radiation detectors to detect levels of light absorption related to the emitted pulses of light, and to produce an output that is proportional to an oxygen saturation level in the blood vessel. The head-mounted member may comprise an eyeglasses frame. The eyeglasses frame may be a binocular eyeglasses frame. The one or more radiation emitters may comprise a light emitting diode. The one or more radiation emitters may comprise a plurality of light emitting diodes configured to emit electromagnetic radiation at two predetermined wavelengths. The plurality of light emitting diodes may be configured to emit electromagnetic radiation at a first wavelength of about 660 nanometers, and a second wavelength of about 940 nanometers. The one or more radiation emitters may be configured to emit electromagnetic radiation at the two predetermined wavelengths sequentially. The one or more radiation emitters may be configured to emit electromagnetic radiation at the two predetermined wavelengths simultaneously. The one or more electromagnetic radiation detectors may comprise a device selected from the group consisting of: a photodiode, a photodetector, and a digital camera sensor. The one or more electromagnetic radiation detectors may be positioned and oriented to receive light reflected after encountering at least one blood vessel of the retina of the eye of the user. The one or more electromagnetic radiation detectors may be positioned and oriented to receive light reflected after encountering at least one blood vessel of the sclera of the eye of the user. The controller may be further configured to cause the plurality of light emitting diodes to emit a cyclic pattern of first wavelength on, then second wavelength on, then both wavelengths off, such that the one or more electromagnetic radiation detectors detect the first and second wavelengths separately. The controller may be configured to cause the plurality of light emitting diodes to emit a cyclic pattern of first wavelength on, then second wavelength on, then both wavelengths off, in a cyclic pulsing pattern about thirty times per second. The controller may be configured to calculate a ratio of first wavelength light measurement to second wavelength light measurement, and wherein this ratio is converted to an oxygen saturation reading via a lookup table based at least in part upon the Beer-Lambert law. The controller may be configured to operate the one or more electromagnetic radiation emitters and one or more electromagnetic radiation detectors to function as a head-mounted pulse oximeter. The controller may be operatively coupled to an optical element coupled to the head-mounted member and viewable by the user, such that the output of the controller that is proportional to an oxygen saturation level in the blood vessel of the user may be viewed by the user through the optical element. The one or more electromagnetic radiation detectors may comprise a digital image sensor comprising a plurality of pixels, wherein the controller is configured to automatically detect a subset of pixels which are receiving the light reflected after encountering at least one blood vessel of the eye of the user, and to use such subset of pixels to produce the output that is proportional to an oxygen saturation level in the blood vessel. The controller may be configured to automatically detect the subset of pixels based at least in part upon reflected light luminance differences amongst signals associated with the pixels. The controller may be configured to automatically detect the subset of pixels based at least in part upon reflected light absorption differences amongst signals associated with the pixels.

DETAILED DESCRIPTION

Referring to FIGS. 2A-2D, some general componentry options are illustrated. In the portions of the detailed description which follow the discussion of FIGS. 2A-2D, various systems, subsystems, and components are presented for addressing the objectives of providing a high-quality, comfortably-perceived display system for human VR and/or AR.

Figure 2A:
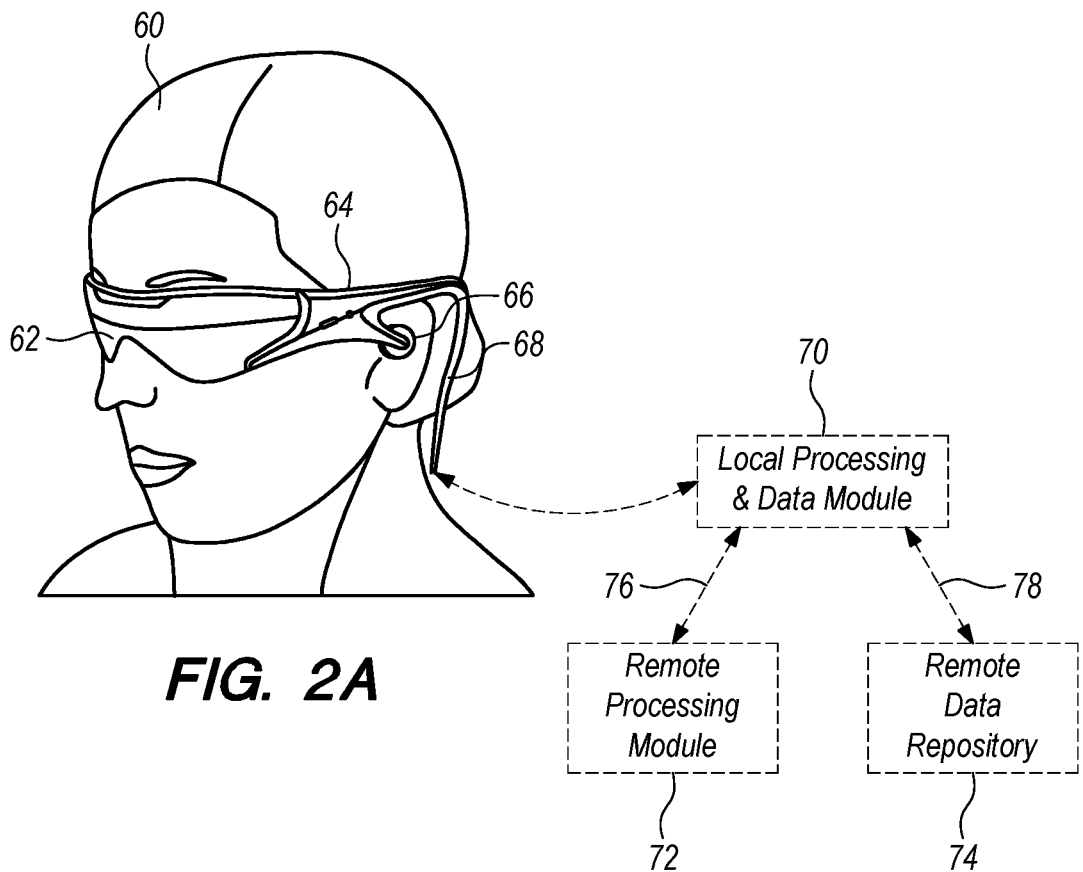
FIGS. 2A-2D illustrate certain aspects of various augmented reality systems for wearable computing applications, featuring a head-mounted component operatively coupled to local and remote process and data components.
Figure 2B:
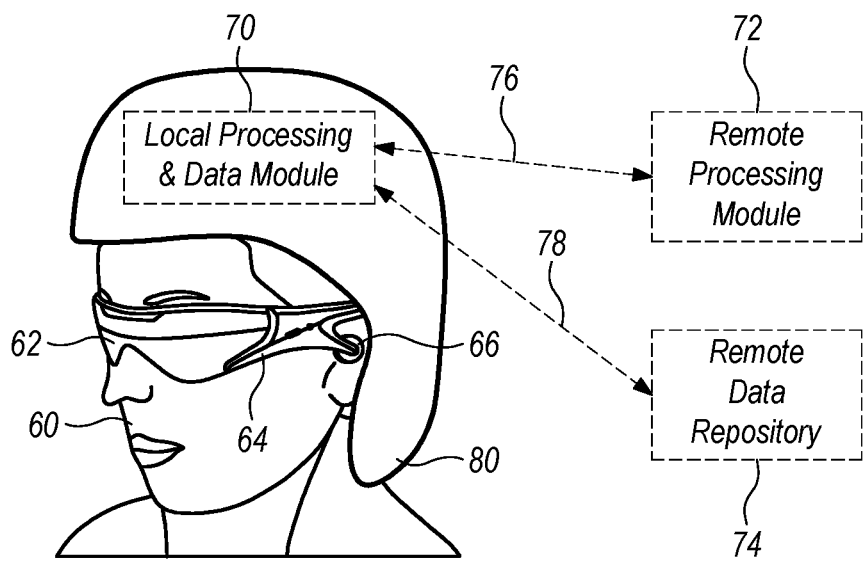
Figure 2C:
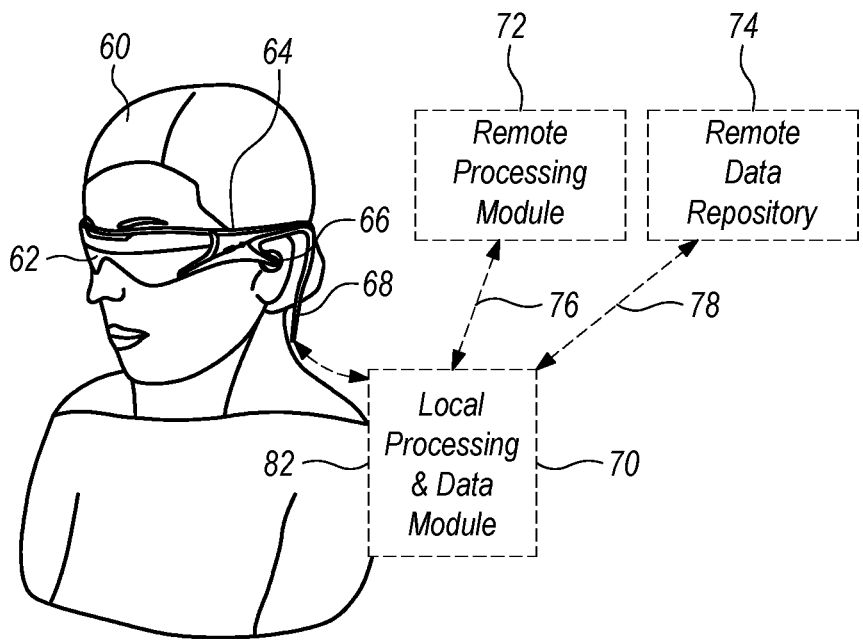
Figure 2D:
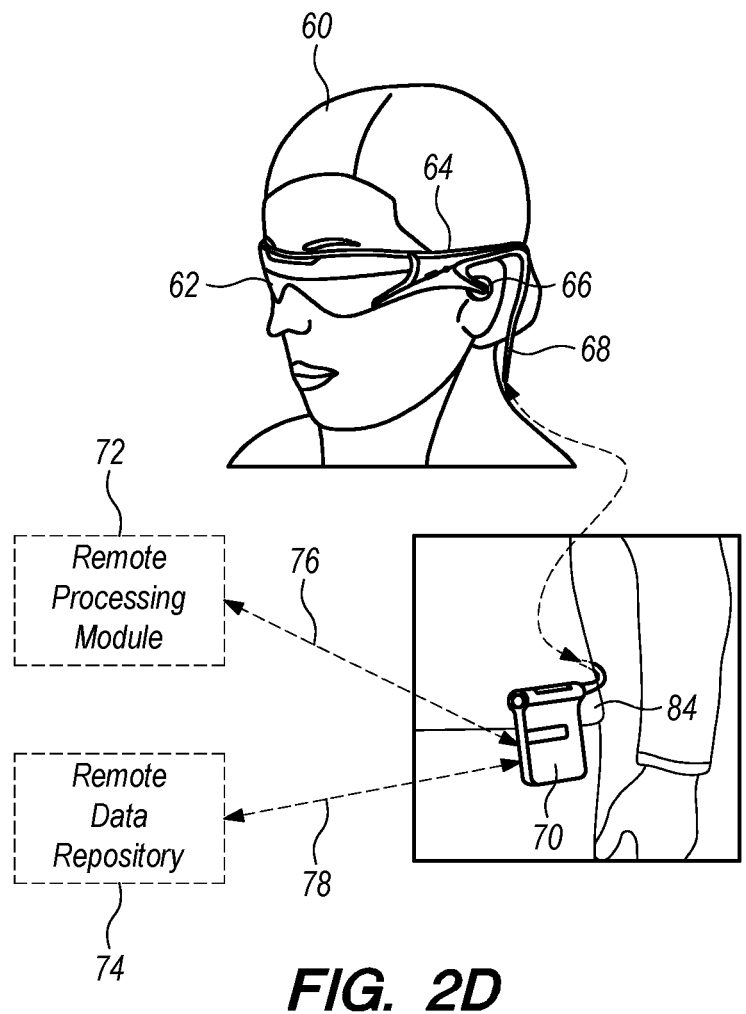

As shown in FIG. 2A, an AR system user (60) is depicted wearing head mounted component (58) featuring a frame (64) structure coupled to a display system (62) positioned in front of the eyes of the user. A speaker (66) is coupled to the frame (64) in the depicted configuration and positioned adjacent the ear canal of the user (in one embodiment, another speaker, not shown, is positioned adjacent the other ear canal of the user to provide for stereo/shapeable sound control). The display (62) is operatively coupled (68), such as by a wired lead or wireless connectivity, to a local processing and data module (70) which may be mounted in a variety of configurations, such as fixedly attached to the frame (64), fixedly attached to a helmet or hat (80) as shown in the embodiment of FIG. 2B, embedded in headphones, removably attached to the torso (82) of the user (60) in a backpack-style configuration as shown in the embodiment of FIG. 2C, or removably attached to the hip (84) of the user (60) in a belt-coupling style configuration as shown in the embodiment of FIG. 2D.

The local processing and data module (70) may comprise a power-efficient processor or controller, as well as digital memory, such as flash memory, both of which may be utilized to assist in the processing, caching, and storage of data a) captured from sensors which may be operatively coupled to the frame (64), such as image capture devices (such as cameras), microphones, inertial measurement units, accelerometers, compasses, GPS units, radio devices, and/or gyros; and/or b) acquired and/or processed using the remote processing module (72) and/or remote data repository (74), possibly for passage to the display (62) after such processing or retrieval. The local processing and data module (70) may be operatively coupled (76, 78), such as via a wired or wireless communication links, to the remote processing module (72) and remote data repository (74) such that these remote modules (72, 74) are operatively coupled to each other and available as resources to the local processing and data module (70).

In one embodiment, the remote processing module (72) may comprise one or more relatively powerful processors or controllers configured to analyze and process data and/or image information. In one embodiment, the remote data repository (74) may comprise a relatively large-scale digital data storage facility, which may be available through the internet or other networking configuration in a "cloud" resource configuration. In one embodiment, all data is stored and all computation is performed in the local processing and data module, allowing fully autonomous use from any remote modules.

Figure 3:
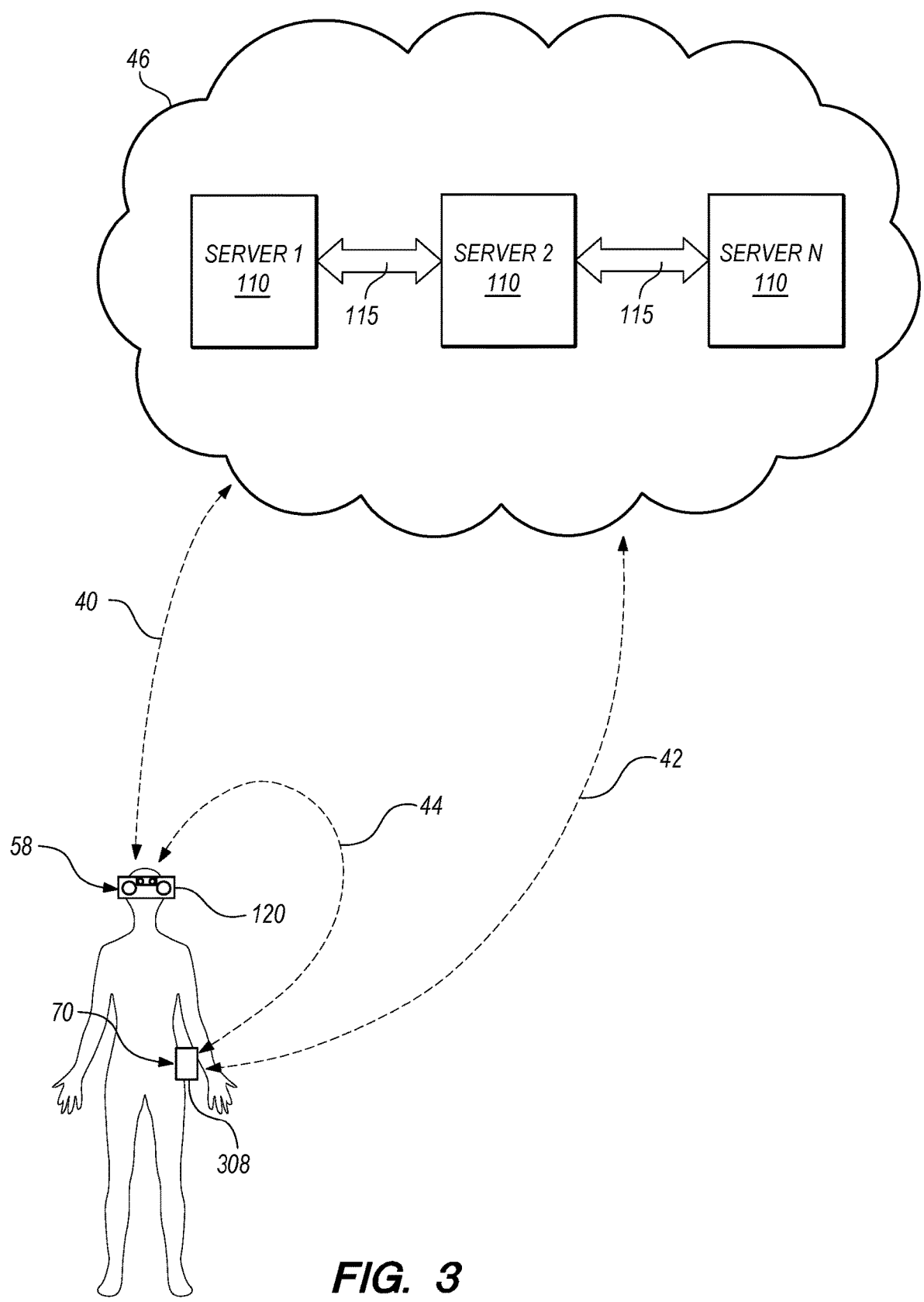
FIG. 3 illustrates certain aspects of a connectivity paradigm between a wearable augmented or virtual reality system and certain remote processing and/or data storage resources.
Figure 4A:
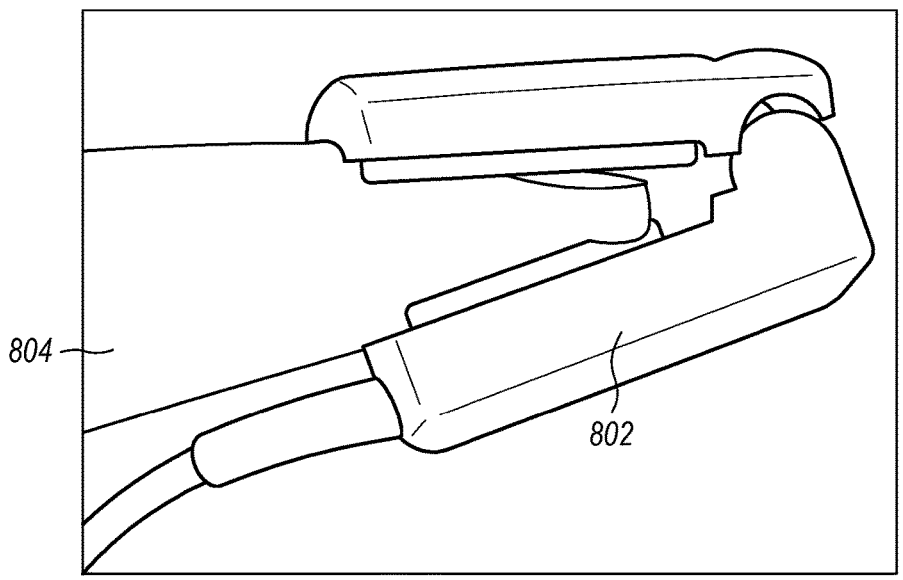
FIGS. 4A-4C illustrate various aspects of conventional pulse oximetry configurations.
Figure 4B:
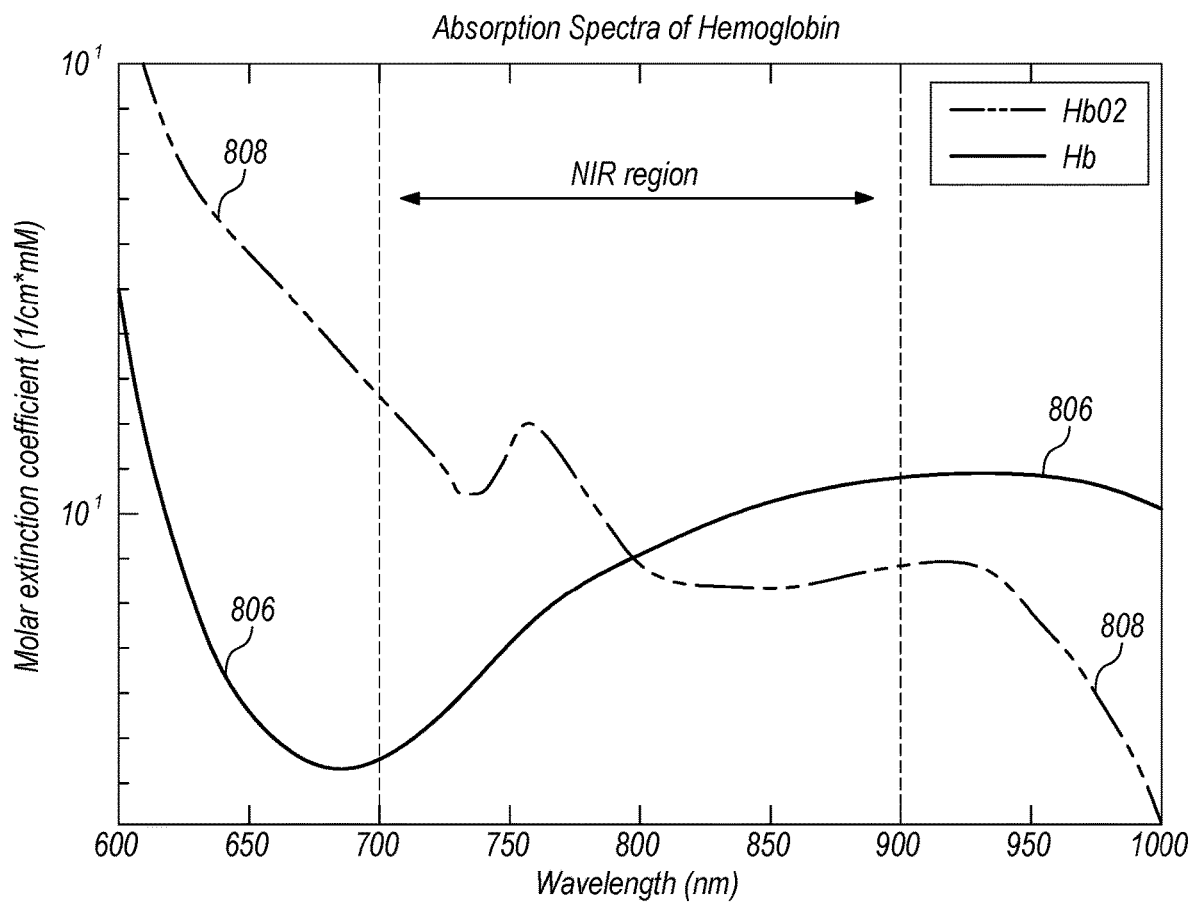
Figure 4C:
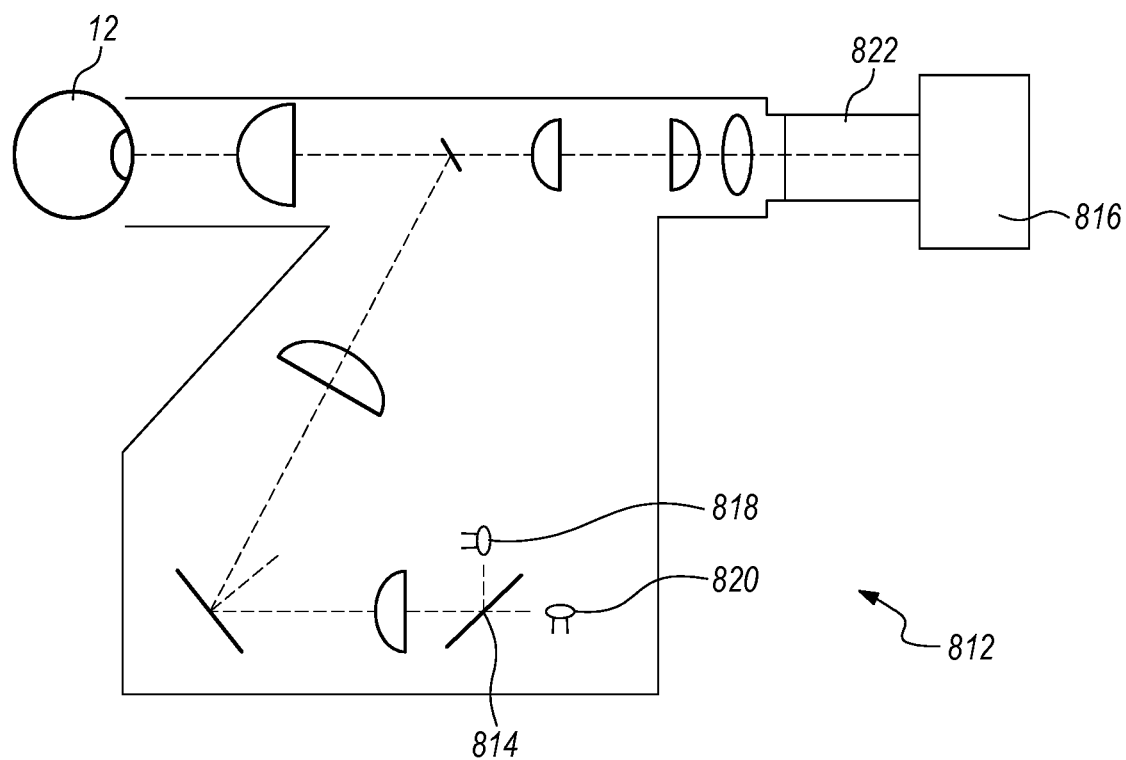

Referring now to FIG. 3, a schematic illustrates coordination between the cloud computing assets (46) and local processing assets, which may, for example reside in head mounted componentry (58) coupled to the user's head (120) and a local processing and data module (70), coupled to the user's belt (308; therefore the component 70 may also be termed a "belt pack" 70), as shown in FIG. 3. In one embodiment, the cloud (46) assets, such as one or more server systems (110) are operatively coupled (115), such as via wired or wireless networking (wireless being preferred for mobility, wired being preferred for certain high-bandwidth or high-data-volume transfers that may be desired), directly to (40, 42) one or both of the local computing assets, such as processor and memory configurations, coupled to the user's head (120) and belt (308) as described above. These computing assets local to the user may be operatively coupled to each other as well, via wired and/or wireless connectivity configurations (44), such as the wired coupling (68) discussed below in reference to FIG. 8. In one embodiment, to maintain a low-inertia and small-size subsystem mounted to the user's head (120), primary transfer between the user and the cloud (46) may be via the link between the subsystem mounted at the belt (308) and the cloud, with the head mounted (120) subsystem primarily data-tethered to the belt-based (308) subsystem using wireless connectivity, such as ultra-wideband ("UWB") connectivity, as is currently employed, for example, in personal computing peripheral connectivity applications.

With efficient local and remote processing coordination, and an appropriate display device for a user, such as the user interface or user display system (62) shown in FIG. 2A, or variations thereof, aspects of one world pertinent to a user's current actual or virtual location may be transferred or "passed" to the user and updated in an efficient fashion. In other words, a map of the world may be continually updated at a storage location which may partially reside on the user's AR system and partially reside in the cloud resources. The map (also referred to as a "passable world model") may be a large database comprising raster imagery, 3-D and 2-D points, parametric information and other information about the real world. As more and more AR users continually capture information about their real environment (e.g., through cameras, sensors, IMUs, etc.), the map becomes more and more accurate and complete.

Figure 1:
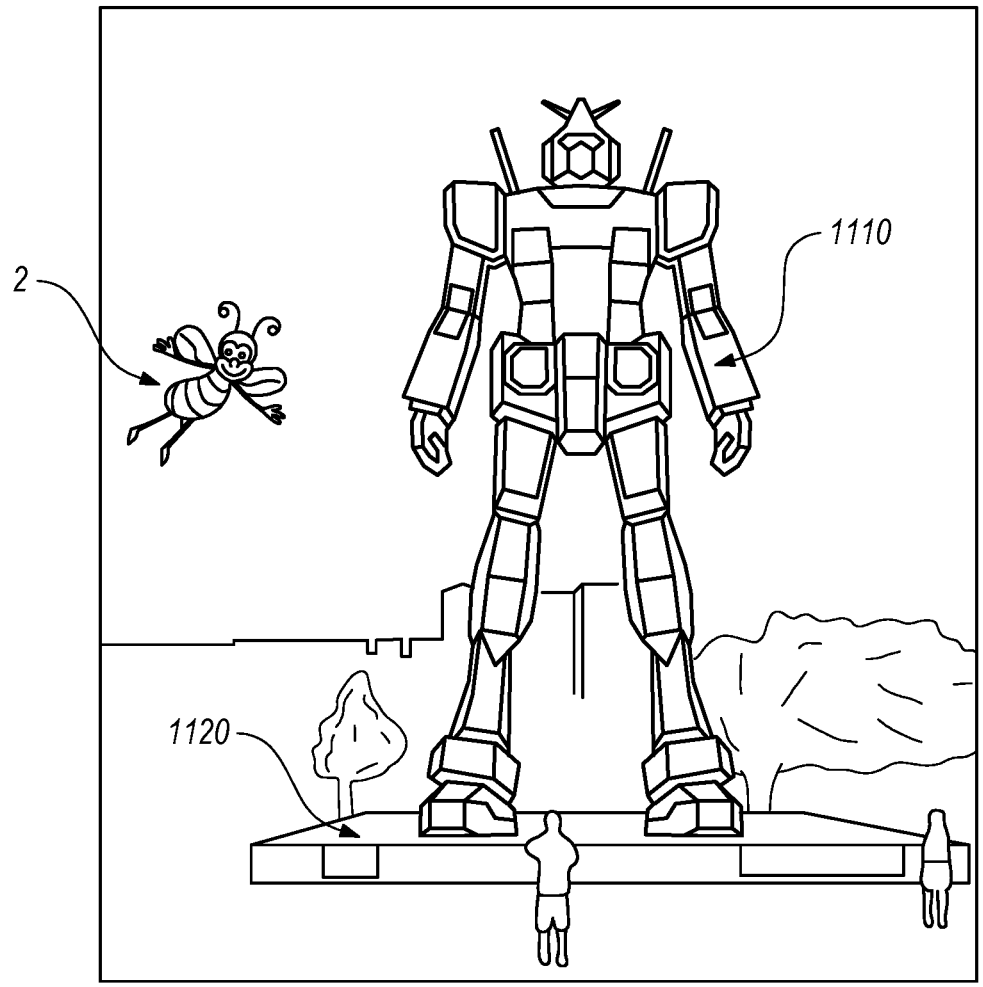
FIG. 1 illustrates certain aspects of an augmented reality system presentation to a user.

With a configuration as described above, wherein there is one world model that can reside on cloud computing resources and be distributed from there, such world can be "passable" to one or more users in a relatively low bandwidth form preferable to trying to pass around real-time video data or the like. The augmented experience of the person standing near the statue (i.e., as shown in FIG. 1) may be informed by the cloud-based world model, a subset of which may be passed down to them and their local display device to complete the view. A person sitting at a remote display device, which may be as simple as a personal computer sitting on a desk, can efficiently download that same section of information from the cloud and have it rendered on their display. Indeed, one person actually present in the park near the statue may take a remotely-located friend for a walk in that park, with the friend joining through virtual and augmented reality. The system will need to know where the street is, wherein the trees are, where the statue is—but with that information on the cloud, the joining friend can download from the cloud aspects of the scenario, and then start walking along as an augmented reality local relative to the person who is actually in the park.

3-D points may be captured from the environment, and the pose (i.e., vector and/or origin position information relative to the world) of the cameras that capture those images or points may be determined, so that these points or images may be "tagged", or associated, with this pose information. Then points captured by a second camera may be utilized to determine the pose of the second camera. In other words, one can orient and/or localize a second camera based upon comparisons with tagged images from a first camera. Then this knowledge may be utilized to extract textures, make maps, and create a virtual copy of the real world (because then there are two cameras around that are registered).

So at the base level, in one embodiment a person-worn system can be utilized to capture both 3-D points and the 2-D images that produced the points, and these points and images may be sent out to a cloud storage and processing resource. They may also be cached locally with embedded pose information (i.e., cache the tagged images); so the cloud may have on the ready (i.e., in available cache) tagged 2-D images (i.e., tagged with a 3-D pose), along with 3-D points. If a user is observing something dynamic, he may also send additional information up to the cloud pertinent to the motion (for example, if looking at another person's face, the user can take a texture map of the face and push that up at an optimized frequency even though the surrounding world is otherwise basically static). As noted above, more information on object recognizers and the passable world model may be found in U.S. patent application Ser. No. 14/205,126, entitled "System and method for augmented and virtual reality", which is incorporated by reference in its entirety herein, along with the following additional disclosures, which related to augmented and virtual reality systems such as those developed by Magic Leap, Inc. of Fort Lauderdale, Fla.: U.S. patent application Ser. No. 14/641,376; U.S. patent application Ser. No. 14/555,585; U.S. patent application Ser. No. 14/212,961; U.S. patent application Ser. No. 14/690,401; U.S. patent application Ser. No. 13/663,466; U.S. patent application Ser. No. 13/684,489; and U.S. Patent Application Ser. No. 62/298,993, each of which is incorporated by reference herein in its entirety.

GPS and other localization information may be utilized as inputs to such processing. Highly accurate localization of the user's head, totems, hand gestures, haptic devices etc. are crucial in displaying appropriate virtual content to the user.

Figure 5:
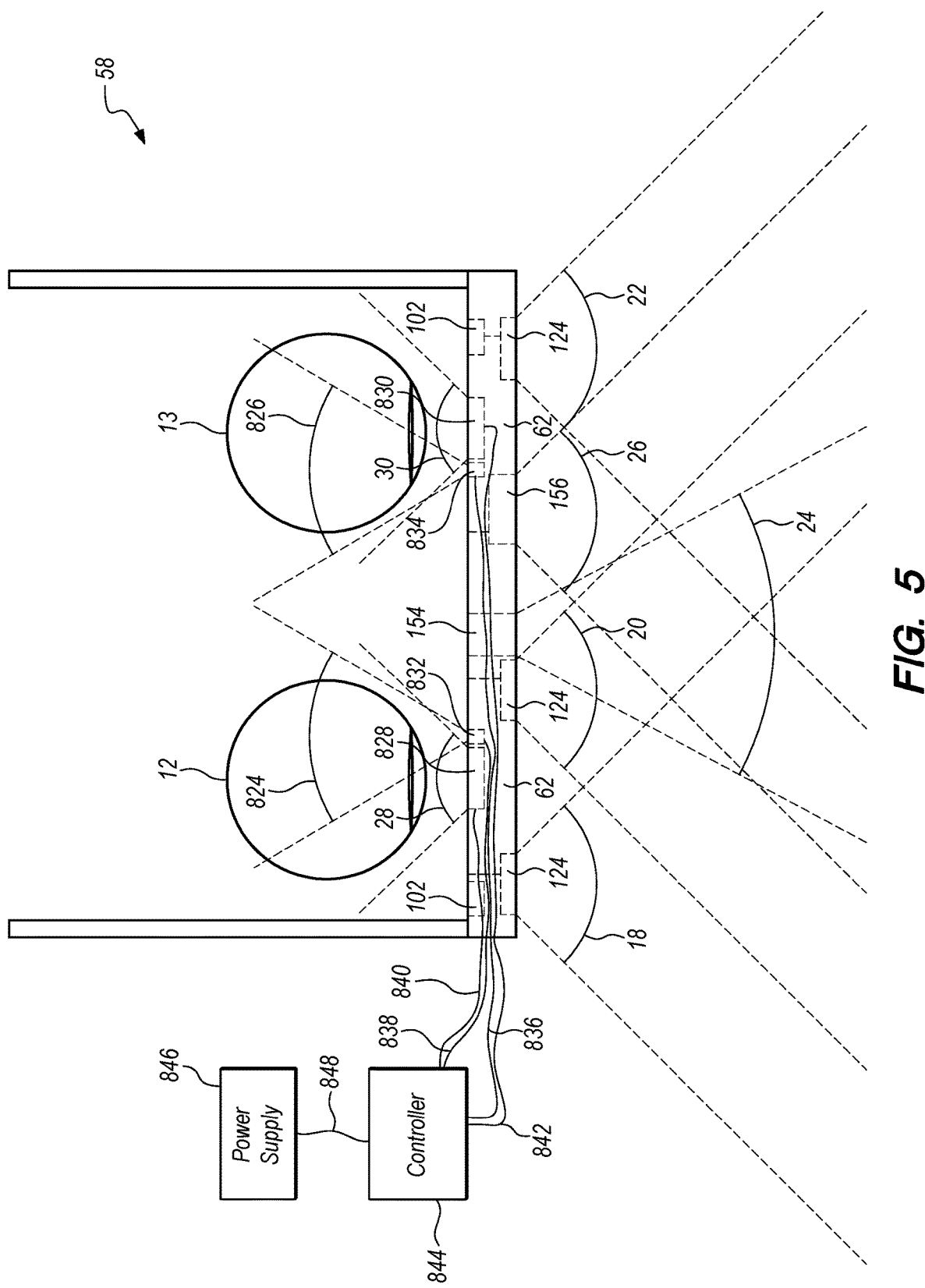
FIG. 5 illustrates various aspects of a wearable AR/VR system featuring integrated pulse oximetry modules.

Referring to FIG. 5, a top orthogonal view of a head mountable component (58) of a wearable computing configuration is illustrated featuring various integrated components for illustrative purposes. The configuration features two display elements (62—binocular—one for each eye) three forward-oriented cameras (124) for observing and detecting the world around the user, each having an associated field of view (18, 20, 22); also a forward-oriented relatively high resolution picture camera (156) with a field of view (26), one or more inertial measurement units (102), and a depth sensor (154) with an associated field of view (24), such as described in the aforementioned incorporated by reference disclosures. Facing toward the eyes (12, 13) of the user and coupled to the head mounted component (58) frame are at least one emitter and at least one detector. The illustrative embodiment shows a redundant configuration, with one detector device (830; associated field of view or field of capture is 30) and one emitter device (834; associated field of irradiation is 826) for the right eye (13), and one detector device (828; associated field of view or field of capture is 28) and one emitter device (832; associated field of irradiation is 824) for the left eye (12). These components are shown operatively coupled (836, 838, 840, 842), such as by wire lead, to a controller (844), which is operatively coupled (848) to a power supply (846), such as a battery. Preferably each emitter (832, 834) is configured to controllably emit electromagnetic radiation in two wavelengths, such as about 660 nm, and about 940 nm, such as by LEDs, and preferably the fields of irradiation (824, 826) are oriented to irradiate targeted tissue comprising oxygenated and deoxygenated hemoglobin, such as the vessels of the sclera of the eye, or the vessels of the retina of the eye; the emitters may be configured to emit both wavelengths simultaneously, or sequentially, with controlled pulsatile emission cycling. The one of more detectors (828, 830) may comprise photodiodes, photodetectors, or digital camera sensors, and preferably are positioned and oriented to receive radiation that has encountered the targeted tissue comprising oxygenated and deoxygenated hemoglobin, so that absorption may be detected and oxygen saturation calculated/estimated. The one or more electromagnetic radiation detectors (828, 830) may comprise a digital image sensor comprising a plurality of pixels, wherein the controller (844) is configured to automatically detect a subset of pixels which are receiving the light reflected after encountering at least one blood vessel of the eye of the user, and to use such subset of pixels to produce the output that is proportional to an oxygen saturation level in the blood vessel. The controller (844) may be configured to automatically detect the subset of pixels based at least in part upon reflected light luminance differences amongst signals associated with the pixels. The controller (844) may be configured to automatically detect the subset of pixels based at least in part upon reflected light absorption differences amongst signals associated with the pixels.

Thus a system is presented for determining oxygen saturation of a user wearing a wearable computing system, such as one for AR or VR, comprising: a head-mounted member (58) removably coupleable to the user's head; one or more electromagnetic radiation emitters (832, 834) coupled to the head-mounted member (58) and configured to emit light with at least two different wavelengths in the visible to infrared spectrum in direction of at least one of the eyes (12, 13) of the user; one or more electromagnetic radiation detectors (828, 830) coupled to the head-mounted member and configured to receive light reflected after encountering at least one blood vessel of the eye of the user; and a controller (844) operatively coupled to the one or more electromagnetic radiation emitters (832, 834) and one or more electromagnetic radiation detectors (828, 830) and configured to cause the one or more electromagnetic radiation emitters to emit pulses of light while also causing the one or more electromagnetic radiation detectors to detect levels of light absorption related to the emitted pulses of light, and to produce an output that is proportional to an oxygen saturation level in the blood vessel. The head-mounted member (58) may comprise an eyeglasses frame. The eyeglasses frame may be a binocular eyeglasses frame; alternative embodiments may be monocular. The one or more radiation emitters (832, 834) may comprise a light emitting diode. The one or more radiation emitters (832, 834) may comprise a plurality of light emitting diodes configured to emit electromagnetic radiation at two predetermined wavelengths. The plurality of light emitting diodes may be configured to emit electromagnetic radiation at a first wavelength of about 660 nanometers, and a second wavelength of about 940 nanometers. The one or more radiation emitters (832, 834) may be configured to emit electromagnetic radiation at the two predetermined wavelengths sequentially. The one or more radiation emitters (832, 834) may be configured to emit electromagnetic radiation at the two predetermined wavelengths simultaneously. The one or more electromagnetic radiation detectors (828, 830) may comprise a device selected from the group consisting of: a photodiode, a photodetector, and a digital camera sensor. The one or more electromagnetic radiation detectors (828, 830) may be positioned and oriented to receive light reflected after encountering at least one blood vessel of the retina of the eye (12, 13) of the user. The one or more electromagnetic radiation detectors (828, 830) may be positioned and oriented to receive light reflected after encountering at least one blood vessel of the sclera of the eye of the user. The controller (844) may be further configured to cause the plurality of light emitting diodes to emit a cyclic pattern of first wavelength on, then second wavelength on, then both wavelengths off, such that the one or more electromagnetic radiation detectors detect the first and second wavelengths separately. The controller (844) may be configured to cause the plurality of light emitting diodes to emit a cyclic pattern of first wavelength on, then second wavelength on, then both wavelengths off, in a cyclic pulsing pattern about thirty times per second. The controller (844) may be configured to calculate a ratio of first wavelength light measurement to second wavelength light measurement, and wherein this ratio is converted to an oxygen saturation reading via a lookup table based at least in part upon the Beer-Lambert law. The controller (844) may be configured to operate the one or more electromagnetic radiation emitters (832, 834) and one or more electromagnetic radiation detectors (828, 830) to function as a head-mounted pulse oximeter. The controller (844) may be operatively coupled to an optical element (62) coupled to the head-mounted member (58) and viewable by the user, such that the output of the controller (844) that is proportional to an oxygen saturation level in the blood vessel of the user may be viewed by the user through the optical element (62).

Figure 6:
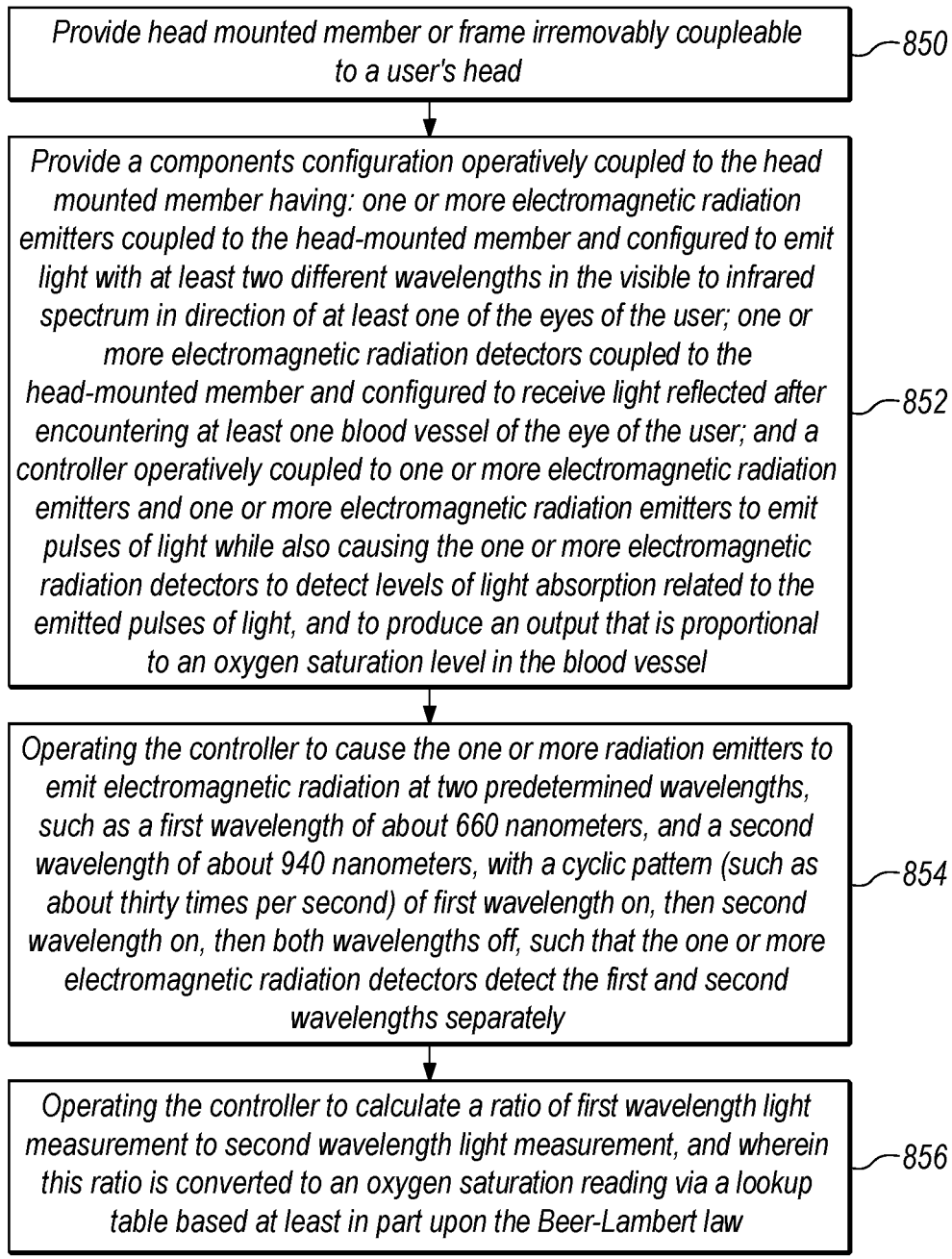
FIG. 6 illustrates various aspects of a technique for using a wearable AR/VR system featuring integrated pulse oximetry modules.

FIG. 6 illustrates various aspects of a technique or method for using a wearable AR/VR system featuring integrated pulse oximetry modules. Referring to FIG. 6, head mounted member or frame removably coupleable to a user's head may be provided (850), and a components configuration may be operatively coupled to the head mounted member, having: one or more electromagnetic radiation emitters coupled to the head-mounted member and configured to emit light with at least two different wavelengths in the visible to infrared spectrum (or in another embodiment, non-visible to infrared) in direction of at least one of the eyes of the user; one or more electromagnetic radiation detectors coupled to the head-mounted member and configured to receive light reflected after encountering at least one blood vessel of the eye of the user; and a controller operatively coupled to the one or more electromagnetic radiation emitters and one or more electromagnetic radiation detectors and configured to cause the one or more electromagnetic radiation emitters to emit pulses of light while also causing the one or more electromagnetic radiation detectors to detect levels of light absorption related to the emitted pulses of light, and to produce an output that is proportional to an oxygen saturation level in the blood vessel (852). The controller may be operated to cause the one or more radiation emitters to emit electromagnetic radiation at two predetermined wavelengths, such as a first wavelength of about 660 nanometers, and a second wavelength of about 940 nanometers, with a cyclic pattern (such as about thirty times per second) of first wavelength on, then second wavelength on, then both wavelengths off, such that the one or more electromagnetic radiation detectors detect the first and second wavelengths separately (854). The controller may be operated to calculate a ratio of first wavelength light measurement to second wavelength light measurement, and wherein this ratio is converted to an oxygen saturation reading via a lookup table based at least in part upon the Beer-Lambert law (856).

In one embodiment, a significant amount of the overall eye-based pulse oximetry activity is done with software operated by the controller (844), such that an initial task of locating vessels (i.e., within the sclera, retina, or other ocular/vascular tissue structure) is conducted using digital image processing (such as by color, grayscale, and/or intensity thresholding analysis using various filters; also may be conducted using pattern and/or shape recognition; the software and controller may be configured to use the intensity of the center of the targeted vessels and the intensity of the surrounding tissue to determine contrast/optical density); with the targeted vessels or other structures identified, emission/detection and processing of detected data (which may include image processing) may be utilized to determine contrast; then the controller (844) may be utilized to calculate density ratios (contrast) and to calculate the oxygen saturation from the density ratios as described above. Vessel optical density ("O.D.") at each of the two or more emitted wavelengths may be calculated using the formula $OD_{vessel} = -\log_{10}(I_v/I_r)$, wherein $OD_{vessel}$ is the optical density of the vessel; $I_v$ is the vessel intensity; and $I_r$ is the surrounding retina tissue intensity. Oxygen saturation (also termed "SO$_2$") may be calculated as a linear ratio of vessel optical densities (OD ratio, or "ODR") at the two wavelengths, such that $SO_2 = ODR = OD_{firstwavelength}/OD_{secondwavelength}$ In one embodiment, wavelengths of about 570 nm (sensitive to deoxygenated hemoglobin) and about 600 nm (sensitive to oxygenated hemoglobin) may be utilized in retinal vessel oximetry, such that $SO_2 = ODR = OD_{600\ nm}/OD_{570\ nm}$; such formula does not account for adjusting the ratio by a calibration coefficient.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and the include plural referents unless the specifically stated otherwise. In other words, use of the articles allow for at least one of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for determining oxygen saturation of a user, comprising:
  a. a head-mounted member removably coupleable to a head of the user;
  b. one or more electromagnetic radiation emitters coupled to the head-mounted member and configured to emit light with at least two different wavelengths in the visible to infrared spectrum in direction of at least one eye of the user and having an associated field of irradiation that includes a retina and a sclera of the eye of the user;

c. one or more electromagnetic radiation detectors coupled to the head-mounted member and configured to receive light reflected after encountering at least one blood vessel of the retina or the sclera of the eye of the user; and d. a controller operatively coupled to the one or more electromagnetic radiation emitters and one or more electromagnetic radiation detectors and configured to cause the one or more electromagnetic radiation emitters to emit pulses of light while also causing the one or more electromagnetic radiation detectors to detect levels of light absorption related to the pulses of light, and to produce an output that is proportional to an oxygen saturation level in the blood vessel by determining a ratio of light having the second wavelength divided by light having the first wavelength detected by the one or more electromagnetic radiation detectors.

2. The system of claim 1, wherein the head-mounted member comprises an eyeglasses frame.

3. The system of claim 2, wherein the eyeglasses frame is a binocular eyeglasses frame.

4. The system of claim 1, wherein the one or more radiation emitters comprises a light emitting diode.

5. The system of claim 4, wherein the one or more radiation emitters comprises a plurality of light emitting diodes configured to emit electromagnetic radiation at two predetermined wavelengths.

6. The system of claim 5, wherein the plurality of light emitting diodes are configured to emit electromagnetic radiation at a first wavelength of about 660 nanometers, and a second wavelength of about 940 nanometers.

7. The system of claim 5, wherein the one or more radiation emitters are configured to emit electromagnetic radiation at the two predetermined wavelengths sequentially.

8. The system of claim 5, wherein the one or more radiation emitters are configured to emit electromagnetic radiation at the two predetermined wavelengths simultaneously.

9. The system of claim 1, wherein the one or more electromagnetic radiation detectors comprises a device selected from the group consisting of: a photodiode, a photodetector, and a digital camera sensor.

10. The system of claim 1, wherein the controller is further configured to cause the plurality of light emitting diodes to emit a cyclic pattern of first wavelength on, then second wavelength on, then both wavelengths off, such that the one or more electromagnetic radiation detectors detect the first and second wavelengths separately.

11. The system of claim 10, wherein the controller is configured to cause the plurality of light emitting diodes to emit a cyclic pattern of first wavelength on, then second wavelength on, then both wavelengths off, in a cyclic pulsing pattern about thirty times per second.

12. The system of claim 1, wherein the ratio is converted to an oxygen saturation reading via a lookup table based at least in part upon the Beer-Lambert law.

13. The system of claim 1, wherein the controller is configured to operate the one or more electromagnetic radiation emitters and one or more electromagnetic radiation detectors to function as a head-mounted pulse oximeter.

14. The system of claim 1, wherein the controller is operatively coupled to an optical element coupled to the head-mounted member and viewable by the user, such that the output of the controller that is proportional to an oxygen saturation level in the blood vessel of the user may be viewed by the user through the optical element.

15. The system of claim 1, wherein the one or more electromagnetic radiation detectors comprises a digital image sensor comprising a plurality of pixels, and wherein the controller is configured to automatically detect a subset of pixels which are receiving the light reflected after encountering at least one blood vessel of the eye of the user, and to use such subset of pixels to produce the output that is proportional to an oxygen saturation level in the blood vessel.

16. The system of claim 15, wherein the controller is configured to automatically detect the subset of pixels based at least in part upon reflected light luminance differences amongst signals associated with the pixels.

17. The system of claim 15, wherein the controller is configured to automatically detect the subset of pixels based at least in part upon reflected light absorption differences amongst signals associated with the pixels.

* * * * *